United States Patent [19]

Ansari et al.

[11] 3,957,856

[45] May 18, 1976

[54] PRODUCTION OF THE CARBOXYLIC ACID OF PERILLYL ALCOHOL

[75] Inventors: Hifzur R. Ansari, Rayleigh; Paul E. Fido, London, both of England

[73] Assignee: Bush Boake Allen Limited, London, England

[22] Filed: Mar. 24, 1975

[21] Appl. No.: 561,320

[30] Foreign Application Priority Data

Apr. 1, 1974 United Kingdom............... 14367/74

[52] U.S. Cl............................. 260/489; 260/566 A; 260/598; 260/631.5
[51] Int. Cl.²......................................... C07C 67/28
[58] Field of Search............................. 260/489, 491

[56] References Cited
FOREIGN PATENTS OR APPLICATIONS
1,183,849   7/1959   France................................ 260/489

*Primary Examiner*—Vivian Garner
*Attorney, Agent, or Firm*—Flynn & Frishauf

[57] ABSTRACT

A novel method for the production of carboxylic acid esters of perillyl alcohol is provided by the pyrolysis of 1,2 diesters of limonene. The reaction is preferably carried out in the liquid phase at temperatures between 200°C and 260°C. or alternatively in the vapour phase at temperatures between 400°C and 450°C. The perillyl ester is separated from the product mixture formed. It may also be converted to other useful compounds e.g., perillyl alcohol and perillaldehyde and its monoxime. The use of an optically active starting material results in the formation of an optically active product.

10 Claims, No Drawings

PRODUCTION OF THE CARBOXYLIC ACID OF PERILLYL ALCOHOL

This invention relates to the production of carboxylic acid esters of perillyl alcohol from 1, 2 diesters of limonene.

These esters and the corresponding alcohol possess a pleasant odour and are useful as ingredients of compounded perfumery compositions. They also find use as intermediates in the synthesis of other terpene chemicals which are of value in the perfumery and flavouring industry.

Perillaldehyde and perillyl alcohol are found in nature as constituents of several essential oils; usually they are found in their optically active form. Several methods for the manufacture of these compounds by synthetic methods have been proposed but as far as we are aware none of these have achieved any commercial success. Perhaps the most effective method available for the synthesis of perillyl alcohol is the pyrolysis of the alcohol, myrtenol, i.e. the compound of the formula

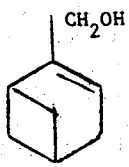

However this method is unsatisfactory in that myrtenol is a relatively expensive raw material and that the perillyl alcohol is produced in a low yield as one of a number of products of the pyrolysis. It should also be noted that as far as we are aware all of these syntheses of perillyl alcohol result in the formation of optically inactive perillyl compounds.

The applicants have now discovered that the esters of perillyl alcohol having the formula

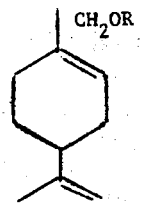

where R is an acyl group having from 2 to 4 carbon atoms, may be prepared by pyrolysing 1,2 carboxylic acid diesters of limonene in the liquid phase for a period of more than four hours and subsequently separating the perillyl ester thus formed from the reaction product mixture.

The liquid phase pyrolysis of limonene diacetate has been proposed in French Patent 1183849 as being a useful method for the preparation of esters of the alcohol carveol i.e. the compound

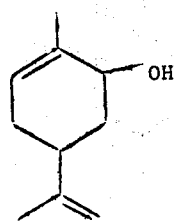

This patent discloses a process in which the 1,2 epoxide of limonene is refluxed with acetic acid and acetic anhydride to yield the 1,2 diacetate of limonene and the excess of these esterification reagents is removed. The diester product of pyrolysed by heating at atmospheric pressure at an elevated temperature. The carvyl acetate is obtained by fractional distillation of the resulting mixture.

Our invention is based on our discovery that the product of the liquid phase pyrolysis depends on the time during which it is carried out, and that in continuing the pyrolysis for some hours a substantial quantity of the perillyl ester is obtained. A third product, 2-acyloxy-p-menth-1(7), 8 diene is obtained in addition to the carveol ester early in the reaction and the overall result if the pyrolysis is continued for long enough can be represented by the following equation

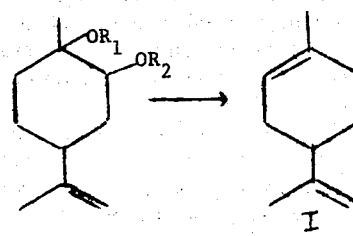

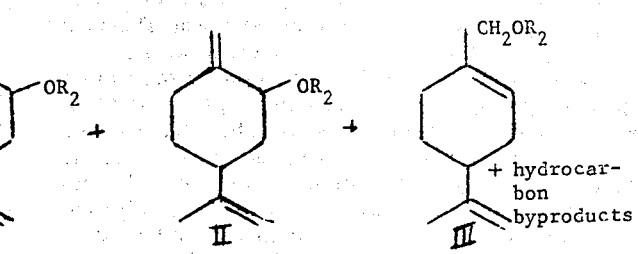

wherein $R_1$ and $R_2$ represent the same or different acyl groups having from 2 to 4 carbon atoms.

More specifically, we have discovered that when this liquid phase reaction is carried out at temperatures of between 200° and 250°C for a period of less than four hours the product comprises compounds of formula I (carvyl esters) and formula II (2-acyloxy-p-menth-1(7), 8 diene, hereinafter referred to as psi-esters. Continuing the pyrolysis would incur the risk of formation of further products, possibly by decomposition of the two just mentioned.

Accordingly from one aspect the invention provides a process for the preparation of compounds of the formula

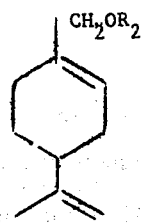

which comprises pyrolysing a compound of formula

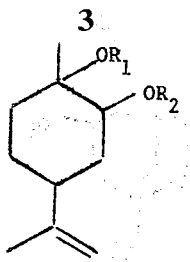

wherein $R_1$ and $R_2$ represent the same or different acyl groups having 2 to 4 carbon atoms in the liquid phase for a period of greater than four hours.

The pyrolysis may be carried out at sub or super atmospheric pressure at a temperature of between 200° and 260°C. Preferably the reaction is carried out at atmospheric pressure at a temperature of between 230° and 250°C. The time of pyrolysis may be from 4 to 18 hours, preferably from 8 to 14 hours. In general, increase in the pyrolysis time favours the production of the desired perillyl compound but as the pyrolysis proceeds, an increasing proportion of the perillyl compound is converted into the corresponding hydrocarbon as a result of deacylation of the mono-esters produced. This conversion increases with increasing temperature and we find that the use of lower temperatures and longer pyrolysis times, favours the formation of the maximum yield of the desired perillyl ester.

Any of the 1,2 diesters of limonene as defined above are useful according to the invention. $R_1$ and $R_2$ may be an acetate, propionate or an n- or iso-butyrate group. In the preferred case $R_1$ and $R_2$ are identical. The most preferred diester for present use is the diacetate.

The pyrolysis can also be carried out in the vapour phase using a temperature in the range 400° to 450°C at substantially atmospheric pressure. The retention time of the vapour in the heated zone is preferably in the range 5 to 20 seconds, more preferably 10 to 15 seconds. It is known in the art of vapour phase pyrolysis to adjust the flow rate and other parameters of the system so as to obtain a retention time of this order using any suitable apparatus.

Accordingly from a second aspect the invention provides a process for the preparation of an ester of the formulation

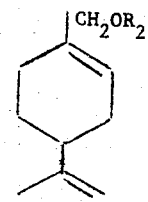

which comprises the pyrolysis of a compound of formula

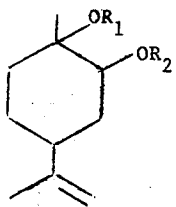

wherein $R_1$ and $R_2$ represent the same or different acyl group having from 2 to 4 carbon atoms at a temperature of from 400° to 450°C for a period of from 5 to 20 seconds.

The products of this pyrolysis are collected in a suitable trap and the desired perillyl ester is separated using conventional techniques such as fractional distillation.

The liquid phase pyrolysis is carried out either batchwise or continuously in a conventional manner. Normally this is achieved simply by refluxing the diester at atmospheric pressure. A carboxylic acid is distilled off during the pyrolysis step together with substantial quantities of low boiling hydrocarbon byproducts. The mono-ester products are retained in the flask and the desired perillyl ester may be separated from this mixture using conventional techniques such as fractional distillation.

We have also discovered that if the limonene diester used in the process of the invention as hereinbefore described is optically active, this optical activity is retained in the perillyl ester product. As far as we are aware this represents the first synthetic method by which an optically active perillyl ester as is found in nature can be prepared. Such processes of preparing an optically active perillyl ester constitute a preferred aspect of the invention.

The 1,2 diesters of limonene which form the starting materials for the processes of the invention are readily prepared from the hydrocarbon, limonene in its optically active form if desired, using techniques well known in the art. Thus conveniently limonene is dissolved in a suitable solvent and treated with a per acid derived from a suitable carboxylic acid at ambient temperature. The product comprises a mixture of the 1.2 hydroxy ester and the 1.2 epoxide of limonene and treatment of this mixture under reflux with an excess of suitable esterifying agent such as a carboxylic acid or a carboxylic acid anhydride; preferably corresponding to the per-acid used in the hydration step, yields the desired 1,2 diester.

The perillyl esters produced by the processes of the invention may be used as odorants themselves or may be converted using the conventional techniques of synthetic organic chemistry to other useful compounds. Thus, perillyl alcohol may be obtained by saponification of an ester with an aqueous base and the alcohol may be oxidised to perillaldehyde using for example, an acidic solution of a dichromate as the oxidising agent. Alternatively, the alcohol can be re-esterified to form other desired esters.

The aldehyde may be condensed with hydroxyl amine to give perillaldehyde monoxime which is widely used as a sweetener.

The invention is illustrated by the following examples:

EXAMPLE I

Preparation of limonene-1, 2-diacetate

Limonene (136 g., 1 mole), methylene chloride (50 g.) and sodium acetate (12 g.) were stirred, while peracetic acid (228 g. of 36% commercial per-acid), was added over 3 hours at 40°C. After 10 hours the reaction mixture was washed with brine, dried and distilled to give:

| | |
|---|---|
| Unchanged limonene | 8 g. |
| Limonene-1, 2-epoxide | 30 g. |
| Limonene-1, 2-hydroxy acetate | 121 g. |
| Residue | 9 g. |

The combined hydroxy-acetate and the epoxide mixture was treated with an excess of acetic anhydride at reflux temperature for 8 hours. The usual work-up followed by distillation gave the required diacetate.

EXAMPLE II

Pyrolysis of limonene-1, 2-diacetate

The diacetate (1245 g., 4.9 moles) and sodium acetate were heated in a flask fitted with a short fenski column for 8 –9 hours at 240°C. During this period, a total of 584 g. of hydrocarbons and acetic acid were collected as distillate. The product retained in the flask was a mixture of mono-esters and was distilled to give the following:

| | |
|---|---|
| cis- and trans-carvyl acetates | 153.0 g. |
| psi-acetate | 102.5 g. |
| Perillyl acetate | 256.0 g. |
| Unchanged diacetate | 128.0 g. |

EXAMPLE III

Vapour phase pyrolysis of Limonene-1,2-diacetate

Limonene-1.2-diacetate (508 g.) was passed through a glass tube (0.25 inches × 4 feet) heated to 450°C, at a rate of 1 c.c. per minute. The pyrolysate was washed with dilute sodium carbonate solution and distilled to give the following fractions:

| Fraction | Description | Boiling range | Weight |
|---|---|---|---|
| 1 | Hydrocarbons | 80 – 112°/ 5 mm | 150 g. |
| 2 | Carvyl acetates and Psi-acetate | 112 – 120°/ 5 mm | 165 g. |
| 3 | Perillyl acetate | | 35 g. |

EXAMPLE IV

Saponification of Perillyl acetate

Perillyl acetate (196 g.) derived from either of the examples mentioned and 30% aqueous sodium hydroxide (60 g.) were refluxed gently with stirring for 4 hours. The oil layer was separated and distilled under reduced pressure to give perillyl alcohol (150 g.) b.P. 80°/ 0.7 mm., $\alpha D^0 + 102.5$.

What we claim is:

1. A process for the preparation of compounds of the formula

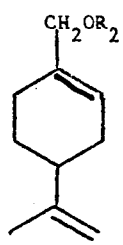

which comprises pyrolysing a compound of the formula

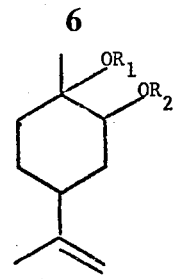

wherein $R_1$ and $R_2$ represent the same or different groups selected from the group consisting of acetyl, propionyl, n-butanoyl and iso-butanoyl; in the liquid phase at a temperature of from 200°C to 260°C for a period of greater than four hours.

2. A process according to claim 1 wherein $R_1$ and $R_2$ are identical.

3. A process according to claim 2 wherein $R_1$ and $R_2$ represent acetyl groups.

4. A process according to claim 3 wherein the pyrolysis is carried out at a temperature of from 230° to 250°C.

5. A process according to claim 3 wherein the pyrolysis is carried out over a period of from 8 to 14 hours.

6. A process for the preparation of a compound of formula

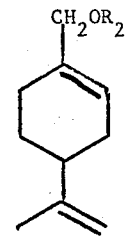

which comprises pyrolysing a compound of formula

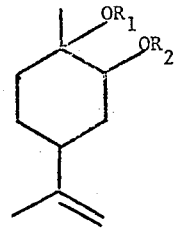

wherein $R_1$ and $R_2$ are the same or different groups selected from the group consisting of acetyl, propionyl, n-butanoyl and iso-butanoyl; in the vapour phase at a temperature of from 400°C to 450°C.

7. A process according to claim 6 wherein the pyrolysis is carried out using a retention time of the vapour in the heated zone of from 5 to 20 seconds.

8. A process according to claim 7 wherein $R_1$ and $R_2$ are identical.

9. A process according to claim 8 wherein the retention time is from 10 to 15 seconds.

10. A process according to claim 7 wherein $R_1$ and $R_2$ both represent acetyl groups.

* * * * *